United States Patent
Girardot et al.

(12) 
(10) Patent No.: US 6,521,179 B1
(45) Date of Patent: *Feb. 18, 2003

(54) STERILIZATION

(75) Inventors: Jean-Marie Girardot, Dunwoody, GA (US); Marie-Nadia Girardot, Dunwoody, GA (US)

(73) Assignee: Biomedical Design, Inc., Marietta, GA (US)

( * ) Notice: Subject to any disclaimer, the term of this patent is extended or adjusted under 35 U.S.C. 154(b) by 42 days.

This patent is subject to a terminal disclaimer.

(21) Appl. No.: 09/635,295

(22) Filed: Aug. 9, 2000

Related U.S. Application Data

(60) Provisional application No. 60/148,427, filed on Aug. 11, 1999.

(51) Int. Cl.[7] .................... A61L 9/00; A61K 38/17; A01N 1/00; A61F 2/24; A61F 2/02
(52) U.S. Cl. ................... 422/28; 422/32; 422/40; 422/292; 530/356; 530/402; 435/1.1; 623/2; 623/11.11; 623/66; 623/915; 623/920
(58) Field of Search .................. 422/1, 28–29, 422/34–36, 40, 256, 292, 307, 901; 530/356, 402; 435/1.1; 623/2, 11, 901, 66, 915, 920

(56) References Cited

U.S. PATENT DOCUMENTS

| | | | |
|---|---|---|---|
| 4,776,853 A | 10/1988 | Klement et al. | 8/94.11 |
| 5,447,536 A | 9/1995 | Girardot et al. | 8/94.11 |
| 5,733,339 A | 3/1998 | Girardot et al. | 8/94.11 |
| 5,911,951 A * | 6/1999 | Girardot et al. | 422/28 |
| 6,117,979 A * | 9/2000 | Hendriks et al. | 530/356 |
| 6,166,184 A * | 12/2000 | Hendriks et al. | 530/356 |

FOREIGN PATENT DOCUMENTS

| | | |
|---|---|---|
| EP | 897942 A1 | 2/1999 |
| WO | WO9727885 | 8/1997 |

OTHER PUBLICATIONS

Lee, J.M. et al., "Crosslinking of tissue–derived biomaterials in 1–ethyl–3– (3–dimethylaminopropyl)–carbodiimide (EDC)", *J. Mater. Sci: Mater, Med.*, pp. 531–541, 1996.

* cited by examiner

*Primary Examiner*—Robert J. Warden, Sr.
*Assistant Examiner*—Monzer R. Chorbaji
(74) *Attorney, Agent, or Firm*—Fitch, Even, Tabin & Flannery

(57) ABSTRACT

Allograft tissue prostheses, as well as tissue valves for replacement of defective heart valves and other tissue-engineered products (TEPs), are effectively sterilized by treatment with a coupling agent known to create amide linkages between amines and carboxylic acids in the presence of a protecting agent. The sterilization treatment preferably employs EDC as a water-soluble coupling agent, plus a water-soluble protecting agent which complexes with potentially reactive amine or carboxyl moieties on the biological tissue, in the optional presence of isopropanol or an equivalent alkanol. One preferred sterilization treatment process uses a buffered aqueous solution where a hydroxymonoamine buffer, such as TRIS plus ethanolamine, provides both the buffering effect and the protecting agents, effectively complexing with potentially reactive carboxyl moieties on the tissue. The treatment is particularly advantageous for sterilizing fresh biological tissue where substantial cross-linking that would alter physical properties of the tissue is undesirable or any tissues or TEPs where a controllable amount of cross-linking is desired.

20 Claims, No Drawings

STERILIZATION

This application claims priority from U.S. application Ser. No. 60/148,427 filed Aug. 11, 1999, the disclosure of which is incorporated herein by reference.

FIELD OF THE INVENTION

This invention relates to sterilization and more specifically to sterilization processes for use with biological materials, such as organ replacements and homografts, which processes exhibit efficacy against difficult-to-kill bacteria and bacterial spores wherein the effect upon the physical properties of the biological material being sterilized is controllable.

BACKGROUND OF THE INVENTION

Sterilization techniques are widely used and important in industries such as food processing and health care. Saturated steam at temperatures above 110° C. has frequently been used to destroy microorganisms, such as microbial spores. Certain articles, particularly those used for health care which consist of or incorporate biological tissue, cannot withstand the temperatures and moisture of steam sterilization, and oftentimes such articles are also considered not to be suitable for sterilization by ionizing radiation. Gaseous sterilants have been developed which function at relatively low temperatures and thus may offer an attractive alternative. Ethylene oxide is a commonly used gaseous sterilant which is often used for medical product sterilization; however, in certain instances, the presence of residual ethylene oxide is considered to be detrimental, even in small quantities. Allografts and other implants containing biological tissue have been sterilized by immersion in antibiotic mixtures, but such processes are very expensive and do not destroy certain bacterial spores and viruses. Accordingly, improved methods of sterilization for medical products that include biological tissue have continued to be sought which would not otherwise significantly alter the physical characteristics of the medical products, particularly allografts and xenografts for which the physical effect upon the medical products should be closely controlled.

Our U.S. Pat. No. 5,911,951 describes an excellent sterilization process for biological tissue by treating with a water-soluble carbodiimide, such as EDC, in the presence of a lower alkanol, such as isopropanol.

SUMMARY OF THE INVENTION

It has now been found that medical products which include biological tissue, e.g. allografts and xenografts is such as replacement organs, ligaments, tendons, vascular grafts and the like, as well as acellular material including items made of extracted collagen or using a process such as that taught in U.S. Pat. No. 4,776,853, can be effectively sterilized by treatment with a bactericidal coupling agent of the type known to create amide linkages between amines and carboxyl moieties in a manner so that there is either no significant change or a closely controllable change in the physical character of the biological material being sterilized. Sterilization treatment is preferably carried out at a temperature above ambient in a buffered solution, that may optionally contain isopropyl alcohol or an equivalent alcohol in an amount effective to promote penetration of said coupling agent into the cells of the microorganisms. The sterilization treatment is carried out in the presence of protecting agents that complex with and protect either residual amine groups or residual carboxyl groups on the proteinaceous biological material that is being treated, thereby carefully controlling the amount of cross-linking thereof so as not to undesirably change the physical characteristics of the resultant biological material. The residuals from such treatment are nontoxic, biocompatible, and water-soluble, so that they can easily be washed off the tissue before packaging or implantation in a human body.

It was surprising to find that biological tissue can be effectively sterilized using coupling agents that create amide bonds, while at the same time either avoiding the occurrence of any significant cross-linking within the biological material itself or alternatively carefully controlling the amount of cross-linking which occurs.

In one particular manner, the invention provides a process for sterilization of biological tissue material, which process comprises treating such material with an aqueous solution containing (a) an amount of a water-soluble coupling agent capable of creating amide bonds that is effective to achieve sterilization and (b) an amount of a protecting agent which is effective to complex with potentially reactive amine or carboxyl moieties on the biological tissue material so as to deter such complexed moieties from taking part in an amide-forming cross-linking reaction and thereby limit the amount of cross-linking, and maintaining such treatment for a time and at a temperature which is sufficient to achieve penetration of said coupling agent into the cells of microorganisms carried by such material and effectively kill such microorganisms.

In another particular manner, the invention provides a process for sterilization of biological tissue, which process comprises treating such material with a protecting agent which is effective to complex with potentially reactive amine or carboxyl moieties on the biological tissue material so as to deter such complexed moieties from taking part in an amide-forming cross-linking reaction and thereby limit the amount of cross-linking, treating such material with a water-soluble coupling agent capable of creating amide bonds that is effective to achieve sterilization, and maintaining such treatment with said coupling agent for a time and at a temperature which is sufficient to achieve penetration of said coupling agent into the cells of microorganisms carried by such material and effectively kill such microorganisms.

In a further particular manner, the invention provides a process of sterilization of biological tissue that has been rendered acellular either before or after cross-linking or that has not been cross-linked.

DETAILED DESCRIPTION OF THE PREFERRED EMBODIMENTS

Medical products which consist of or incorporate biological tissue require sterilization prior to packaging or prior to implantation into a patient, and for certain products, the sterilant should be one that leaves no undesirable residue and that either does not change the physical characteristics of the medical product or only changes it in a carefully controllable manner. For example, for allografts, changes in the structure or the rigidity of the biological tissue are considered detrimental and to be avoided. Allografts, sometimes referred to as homografts, include replacement organs and connective tissues, e.g. cartilage, tendons, ligaments, bone, and muscle tissue, and are generally desirably transplanted into a receiving patient without change in structure or character. On the other hand, certain medical products which include animal tissue, such as prosthetic tissue valves for heart valve replacement, e.g. porcine aortic valves or tissue valves constructed from bovine pericardium, may have been previously fixed, i.e. cross-linked, to carefully provide them with a character and flexibility desired for long term operation. Accordingly, any change to such carefully tailored physical characteristics, as by rigidifying the tissue, may be considered to constitute an undesirable alteration of the product. Still other tissue-engineered products may desirably have a variable duration of resorption in instances where it is desired that the body remodel the product following implantation.

In the foregoing context, once it was discovered that amide-creating coupling agents could be effectively used to sterilize articles by completely inactivating microorganisms and spores, it was decided to investigate if such a sterilization treatment could be adapted to sterilizing allografts and other such engineered tissue products that include mammalian biological tissue. It was surprisingly found that the potentially accompanying undesirable cross-linking of the proteinaceous biological tissue could be minimized or carefully controlled by carrying out the sterilization treatment in the presence of protective agents that would temporarily or permanently complex with the potentially reactive amine or carboxyl moieties on the proteinaceous material and prevent extensive cross-linking that would otherwise change the physical properties of the biological material, as by rigidifying it.

The term "coupling agent" is herein used to refer to a chemical reagent that facilitates the formation of amide bonds. Such bonds may be formed between reactive amines and reactive carboxyls on enzymes or proteins; they may also be formed with and between the reactive carboxyl or amine moieties located on and within bioprosthetic tissue as taught in U.S. Pat. No. 5,733,339, the disclosure of which is incorporated herein by reference. Those having skill in peptide synthesis and related arts will be familiar with such reagents, e.g. water-soluble carbodiimides; a list of such coupling agents is found in the book: Bioconjugate Techniques by Greg T. Hermanson published by Academic Press 1996. This sterilization process which destroys bacteria and spores by treatment with such coupling agents is promoted when carried out in the presence of a $C_2$ to $C_4$ alkanol. For purpose of this application, sterilization is considered to be achieved when the conditions of treatment achieve at least a log 6 reduction in bacteria content, or would so reduce a standard bacteria sample.

A water-soluble coupling agent is preferably chosen so the treatment of biological tissue materials can be effected in aqueous solution. The preferred coupling agent is 1-ethyl-3(3-dimethyl aminopropyl)carbodiimide hydro-chloride (EDC); alternative suitable coupling agents include other water-soluble carbodiimides such as 1-cyclohexyl-3-(2-morpholinoethyl) carbodiimide, N,N'-carbonyldiimidazole, Woodward's Reagent K and mixtures of such carbodiimides.

Concentrations of the coupling agent can be varied within certain limits, and lower concentrations may be effectively employed if the coupling agent is used in combination with a lower alkanol. When used without an accompanying lower alkanol, the coupling agent is preferably used in a concentration between about 25 millimolar (mM) and about 150 mM; however, often concentrations between about 35 mM and about 70 mM are employed, which are considered effective to destroy all commonly encountered bacteria and spores at temperatures of between about 35° C. and 55° C. Duration of sterilization treatment is usually for at least about 6 hours and preferably at least about 12 hours; however, treatment for 24 hours is common.

The solution may optionally contain up to about 30 volume % of a $C_2$ to $C_4$ alkanol, e.g. ethanol or isopropanol, or an equivalent alcohol; by volume % is meant volume of alcohol relative to volume of solution. Such lower alkanol is believed to assist the coupling agent in effectively penetrating the cell walls of the bacteria, spores or other microorganisms. When an alkanol is used, at least about 10% is used, and between about 15% and about 25% of isopropanol is commonly employed, and the coupling agent may be used at a concentration of only about 5 mM–15 mM although 25 mM may be conveniently used.

The protecting agent may be one which complexes with the reactive amine moieties and/or with the reactive carboxyl moieties that are present on the biological tissue. Advantage has heretofore been taken of the presence of these potentially reactive moieties to stabilize prostheses which include animal tissue, and this stabilization process is commonly referred to as "fixing". Glutaraldehyde has commonly been used as a fixation reagent, and other fixation techniques have employed polyepoxide cross-linking or photo-oxidation. More recently, fixation processes of the types detailed in U.S. Pat. Nos. 5,447,536 and 5,733,339, the disclosures of which are incorporated herein by reference, have been proved to have various advantages. It has now been found that, by complexing protecting agents with these potentially reactive moieties, the amount of cross-linking that occurs in the proteinaceous biological tissue can be minimized or closely controlled, while surprisingly not significantly adversely affecting the bactericidal effect of a sterilization treatment utilizing EDC or an equivalent.

Such a protecting agent can be included in the solution used for the sterilization treatment, or the biological tissue material to be sterilized may be pretreated with the protecting agent. If such pretreatment is used, a slightly lower concentration of the protecting agent may be adequate, inasmuch as there will be greater opportunity for complexing to take place prior to exposure of the proteinaceous material to the coupling agent. Generally, if such pretreatment is employed, the sterilants will then be later added to the solution; however, some blocking agents will link to the tissue so rinsing can take place before sterilizing as mentioned hereinafter.

Potentially reactive amine moieties that are present on the proteinaceous material can be effectively blocked before sterilization with certain protecting agents, such as N-hydroxysulfosuccinimide acetate (sulfo-NHS acetate), acetic anhydride, maleic anhydride and citraconic anhydride, after which rinsing can be effected prior to sterilization. An alternative approach is to use monocarboxylic acids, such as hydroxyproline, acetic acid and propionic acid, as protecting groups that will, in the presence of a coupling agent such as a carbodiimide, preferentially form amide linkages with the active amine moieties, thereby preventing these moieties from forming cross-links with carboxylate groups elsewhere on the proteinaceous material during sterilization. However, when monocarboxylic acids are used as the protecting groups, it may be desirable to employ somewhat greater concentrations of the coupling agent because some of the coupling agent may be diverted from its primary sterilization function.

Instead of complexing the amine moieties, a protecting agent can be chosen to complex the carboxyl moieties. Monoamines which will react with the carboxylic groups can be used, and selection of a hydroxyl monoamine, e.g. ethanolamine or propanolamine, may be preferred. A particularly preferred protecting agent is a combination of ethanolamine and tris(hydroxymethyl)aminomethane (TRIS); TRIS serves two functions because it is also a known buffer that is useful for inclusion in aqueous solutions at physiological pH, although ethanolamine or propanolamine could be used alone as either is capable of serving as both a buffer and a blocking agent. In addition, the hydroxyl groups carried by protecting agents such as TRIS increase the hydrophilicity of the biological tissue and have the effect of rendering it less thrombogenic.

When the protecting agent is included as a part of the aqueous sterilization treatment solution, it is generally employed at a concentration between about 25 mM and about 200 mM, preferably at a concentration between about 50 and about 150 mM, and more preferably at a concentration between about 80 mM and about 120 mM. When pretreatment of the biological tissue material with the protecting agent is employed, the protecting agent, e.g. acetic anhydride or ethanolamine, may generally be used at a concentration between about 5 mM and about 50 mM in an aqueous solution, and preferably at a concentration of at least about 10 mM and, more preferably, at least about 20 mM. When pretreatment is used, it is carried out at least about 5 hours and preferably at least about 12 hours prior to the sterilization treatment because the reagent needs to penetrate the tissue for the chemical reaction to occur.

Reaction conditions for the sterilization process may vary somewhat depending on the specific coupling agent employed. In general, sterilization treatment is carried out in an aqueous buffer solution selected from among those that are well known to those of ordinary skill in this art. Examples of suitable buffers include, but are not limited to, N-2-hydroxyethylpiperazine-N'-ethanesulfonic acid (HEPES) and 3-(N-morpholino)propanesulfonic acid (MOPS), and the like. As earlier indicated, it is possible to use TRIS as a protecting agent for the potentially reactive carboxylate groups, preferably in combination with ethanolamine, in which case it will serve the dual function of a buffer. Under these circumstances, it may be desirable to use TRIS at a concentration between about 50 and about 100 mM, with about the same concentration of ethanolamine.

The pH and concentration of the buffered solution also may vary, again depending upon the coupling agent employed. All solutions used are preferably filtered through 0.45 µm or smaller filters before use. Preferably, the buffer concentration and pH are chosen to provide an effective sterilization environment while being the least harmful to biological tissue material; this will generally be a physiological pH. For example, with EDC as the coupling agent, the pH of the solution employed is usually between about 6.0 and about 7.0. The temperature of the sterilizing solution is usually maintained between about 25° C. and 55° C., although higher temperatures, i.e. at least 35° C., are often used when an optional alkanol is not included. Preferably, sterilization is carried out between 35° C. and 45° C. for a suitable increment of time; duration is shorter or longer dependent upon the concentration of coupling agent. Generally, the higher the concentration of coupling agent that is employed, the shorter will be the duration of treatment necessary to achieve effective sterilization; however, sterilization treatment is generally carried out for at least about 10 hours. Moreover, the inclusion of about 20 volume % of a lower alkanol can also somewhat shorten the needed duration of treatment. For example, in the absence of a lower alkanol, effective sterilization can be achieve; at a combination of concentration and duration equal to about 500–600 millimole hours. Thus, a treatment with about 25 millimoles of coupling agent for about 24 hours, or alternatively, treatment with 50 mM of coupling agent for about 12 hours, would meet this criterion. However, if for example 20% of isopropanol is included in the sterilization solution, treatment with 25 millimolar EDC for a period of even 3 hours, i.e. 75 millimole-hours, would be expected to achieve sterilization. Generally, the sterilization condition set forth in the aforementioned '951 patent are believed to be equally applicable here, particularly from the standpoint of EDC concentration and duration of treatment. On the other hand, treatment for a period of about 24 hours is generally convenient for processing and is often used.

As indicated above, the sterilization treatment method is considered to be particularly useful for sterilizing allografts, such as a replacement ligament, tendon, bone, meniscus, vascular graft, heart valve or bioengineered tissue product having controlled resorption, as well as replacement organ components, such as heart valves, which have been made from animal tissue that has been suitably fixed so as to have desired physical properties. Prior to sterilization such material is first desirably rinsed with cold saline.

Subject to the considerations mentioned above, the biological tissue material being sterilized is usually maintained in contact with the sterilization solution for about 5 to 72 hours; the treatment is potently bactericidal, effectively inactivating even hard-to-kill bacteria and spores. However, because of the presence of the protecting agent, this sterilization treatment either does not significantly change the physical properties of the bioprosthetic tissue or changes it in a carefully controlled manner. Fresh tissue which has not previously been fixed, i.e. cross-linked, becomes only minimally, or alternatively controllably, cross-linked as a result of treatment, as can be seen by measurement of its shrinkage temperature or its resistance to enzymatic digestion, and thus either retains its desired physical properties or has them change somewhat in a carefully controlled manner. For example, when bioengineered tissue products are being treated, the resistance to cross-linking, as seen particularly during collagenase digestion testing, could be modulated to meet specific criteria an increase in shrinkage temperature of not more than about 2° C. will usually be effected.

The present invention is further described by the examples that follow. These examples are not to be construed as limiting in any way either the spirit or the scope of the present invention.

Items which are to be implanted in the human body are required to be sterilized in a manner to effectively destroy all microorganisms. Due to the unique applications of liquid chemicals for use in sterilization processes, it is necessary to be vigilant in detecting, screening and testing microorganisms which could pose significant resistance to the sterilization process. Examples of reference microorganisms which have previously demonstrated high resistance to liquid chemical sterilants are: the spores of *Bacillus subtilis, Clostridium sporogenes, Bacillus pumilus, Chaetonium globosom* and *Microascus cinereus*, and representative vegetative cells, such as *Mycobacterium chelonae, Methylbactrium extorquens* and *Trichosporon aquatile*. Of the foregoing, the most resistant may be the spores of *Bacillus subtilis*.

The preferred coupling agent that is used in the following examples is 1-ethyl-3(3-dimethyl aminopropyl) carbodiimide hydrochloride (EDC), which is commercially available. Peptone water is prepared by dissolving 1g of Bacto Peptone in 1 liter of de-ionized water, and the solution is then filtered into sterile bottles using sterile 0.2 micron filters. Coupling agents and/or protecting agents are solubilized in 10 mM HEPES buffer containing 0.85% of sodium chloride, pH 6.5 (HEPES buffer) or in 10 mM TRIS buffer containing 0.85% sodium chloride, pH 6.5 (TRIS buffer). Concentrations are expressed as mM (number of millimoles of chemical for each liter of solution), or as % (grams per 100 ml of solution). Temperatures are in ° C. (degrees Celsius), with room temperature being about 20–25°.

When porcine aortic roots that are fixed are employed, they are cross-linked according to the method described in U.S. Pat. No. 5,447,536 or glutaraldehyde-fixed or cross-linked or fixed with any other method used to preserve tissue. After fixation, the tissue is stored in 10 mM HEPES, 0.85% NaCl, 20% isopropyl alcohol, pH 7.4, at 4° C. The sterility tests described in the following examples are conducted in the presence of bovine pericardium or porcine heart valve tissue. After such tissue is inoculated with microorganisms for test purposes and then submitted to sterilization, the solution is filtered through a 0.45 micron filter attached to a funnel (filter funnel). The tissue is washed for 20 minutes in a reciprocating shaker in the presence of peptone water containing Tween 80 in order to extract all indigenous spores or microorganisms from the tissue. This solution is then filtered through the same respective filter. The filters are then rinsed with peptone water to eliminate residual chemicals on the membrane that may prevent growth of the organisms tested. The membrane filters are incubated on solid agar TSA plates (Millipore) at about 32° to 33° C., e.g. 32.5° C. All microbiological testing is performed in a biological laminar flow hood to prevent contamination. The shrinkage temperature tests and the resistance to collagenase digestion tests are conducted as described in the '536 patent.

EXAMPLE 1

A sterilization process is carried out using *Bacillus Subtilis* (ATCC 9372)spores (~$10^6$) inoculated in sterile cups which contain cross-linked porcine heart valve leaflets fixed by a process according to U.S. Pat. No. 5,447,536. A 10 mM HEPES, 0.85% NaCl, pH 6.5 solution containing EDC and 100 mM ethanolamine in the presence of 20% isopropyl alcohol is added. EDC is present at 25 mM, 50 mM and 70 mM. The cups and leaflets are incubated at 40° C. for 1, 3 and 5 days of treatment. The solutions are then filtered and the leaflets washed in a shaker as described hereinbefore. The filters are incubated for up to 7 days (incubation duration) at about 32–33° C. using Trypticase Soy Agar (TSA) plates. There is complete kill after one day in respect of all three concentrations of EDC. The results demonstrate that the spores of *Bacillus subtilis* are inactivated with this method of sterilization in the presence of porcine aortic valve leaflets. The leaflets remain flexible and show no noticeable physical change.

Samples of cross-linked porcine aortic root tissue that had been pretreated with either acetic anhydride or with a mixture of TRIS and isopropylamine were effectively sterilized using EDC in the absence of a lower alkanol. The efficacy of EDC sterilization of bovine pericardium tissue in the presence of TRIS has also been demonstrated.

EXAMPLE 2

To specifically determine the effect this sterilization process may have on shrinkage temperature of biological tissue, fresh bovine pericardial tissue is sterilized using 25 mM EDC in 10 mM HEPES, 0.85% NaCl, 20% isopropyl alcohol, pH 6.5, at 40° C. for 24 hours. The tissue is dissected, and the thermal denaturation or shrinkage temperature is determined for fresh control samples and for sterilized samples, as described in the '536 patent. The results are presented in Table A and demonstrate that this sterilization method has some effect on the shrinkage temperature of the tissue.

TABLE 1

| SAMPLES | DENATURATION TEMPERATURE (° C.) |
|---|---|
| Fresh pericardium | 68.5° ± 0.2 |
| Sterilized pericardium | 74.2° ± 0.05 |

It can be seen from Table 1 that the shrinkage temperature of fresh bovine pericardium tissue changes somewhat after sterilization. Although this is substantially less than would be the change if fresh bovine pericardium tissue were purposely subjected to fixing in accordance with the examples in the '339 patent (where the shrinkage temperature of fresh pericardium tissue might reasonably be raised to about 85° C.), it is still a substantial raise of nearly 6° C., which might very likely be undesirable for allografts. However, a more sensitive test for the determination of the degree of cross-linking is resistance to collagenase digestion.

Experiments are carried out which show that the addition of amine or carboxyl-reactive cross-linking blockers during the sterilization of collagenous material in the presence of EDC/IPA results in tissue having a controllable degree of cross-linking that can be varied, as desired, by varying the concentrations of different blockers. These results are demonstrated by testing to determine both resistance to collagenase digestion and resistance to thermal denaturation. By using different blocking agents and/or different concentrations of the blocking agents during sterilization, it can be shown that tissue can be made "fully" resistant to collagenase digestion, i.e. similar to present cross-linked tissue, not resistant, i.e. similar to fresh tissue, or with different desired degrees of collagenase resistance. This biocompatible sterilization technique is considered to be particularly valuable in tissue engineering where a variable duration of resorption to permit remodeling of the construct by the human body is frequently desirable. Thus, this method is considered to be particularly useful to sterilize proteineous material where substantially no addition of cross-links is desirable or where a controllable degree of cross-linking-is desirable for matching to a particular function in the human body following implantations.

EXAMPLE 3

Fresh porcine pericardium was incubated in parallel experiments using the following buffers in the presence or absence of 25 mM EDC and 20% isopropyl alcohol at pH 6.5 for 24 hours at 40° C.

| Solution A. | HEPES 10 mM, NaCl 60 mM and $NH_4Cl$ 50 mM. |
| Solution B. | HEPES 10 mM, NaCl 70 mM and hydroxyproline 40 mM. |
| Solution C. | TRIS 50 mM and NaCl 70 mM. |
| Solution D. | HEPES 10 mM, ethanolamine 50 mM and NaCl 60 mM. |
| Solution E. | TRIS 50 mM, ethanolamine 50 mM and NaCl 20 mM. |
| Solution F. | Control: HEPES 10 mM, NaCl 110 mM. |

Solutions A, C, D and E contain carboxyl-reacting blocking agents, while Solution B contains an amine-reacting blocking agent. Solution F is a control buffer without any blocking agent.

The stability of the sterilized tissue to thermal denaturation (shrinkage temperature) was first tested as carried out in Example 2. The test results are set forth in the table which follows:

TABLE 2A

| SOLUTIONS | CONDITIONS | THERMAL DENATURATION mean +/- SEM (n = 3) |
|---|---|---|
| A | NH$_4$Cl | 68.3 +/- 1.3 |
| B | Hydroxyproline | 70.2 +/- 0.5 |
| C | TRIS | 72.7 +/- 0.3 |
| D | Ethanolamine | 68.7 +/- 0.5 |
| E | TRIS + Ethanolamine | 67.5 +/- 0.8 |
| F | HEPES Control | 73.2 +/- 0.4 |
| G | Fresh Tissue | 68.2 +/- 0.2 |

For comparisons, the thermal denaturation temperature of porcine pericardium cross-linked either with glutaraldehyde or with EDC+Sulfo-NHS is about 87° C.

The results of thermal stability indicate that NH$_4$Cl ethanolamine and TRIS+ethanolamine are the most effective cross-linking blocking agents, resulting in thermal denaturation similar to that of fresh pericardium. Greater increases in thermal stability occur in the presence of TRIS alone or hydroxyproline, indicating some cross-linking of the tissue carbonyl and amine groups and that TRIS (at 50 mM) is not as effective as others in blocking cross-linking. There is no change in the thermal stability of pericardium specimens incubated in the absence of EDC.

Fresh tissue is very susceptible to collagenase digestion while cross-linked tissue is highly resistant to collagenase degradation. Pieces of the porcine pericardium (1×1 cm) which had been sterilized as described were dried in air overnight and weighed. They were then incubated at 37° C. in the presence of 220 units of collagenase Type VII from Clostridium histolyticum (Sigma C-0773). After 24 hours, the pericardium samples were removed from the solution, washed in normal saline solution, dried overnight and weighed. The percentage of tissue digested was then calculated, and the results are presented in Table 2B.

TABLE 2B

| SOLUTIONS | CONDITIONS | COLLAGENASE DIGESTION % WEIGHT DIGESTED mean +/- SEM (n = 3) |
|---|---|---|
| A | NH$_4$Cl | 10.5 +/- 1.1 |
| B | Hydroxyproline | 15.5 +/- 1.8 |
| C | TRIS | 3.3 +/- 0.5 |
| D | Ethanolamine | 19.7 +/- 2.7 |
| E | TRIS + Ethanolamine | 42.4 +/- 4.3 |
| F | HEPES Control | 2.6 +/- 0.3 |
| G | Fresh Tissue | 80.4 +/- 1.1 |

The results of collagenase digestion show that sterilization in the presence of 50 mM TRIS alone does not provide as much protection from cross-linking of proximal carboxyl and amine moieties as sterilization in the presence of NH$_4$Cl, hydroxyproline or ethanolamine, which provide more protection than TRIS or the HEPES control, while the greatest protection is obtained with a combination of TRIS plus ethanolamine. The reason for the rather poor protection in the presence of TRIS alone may be due to steric hindrance (i.e., the TRIS molecule may not be able to effectively reach carboxyl moieties located within the collagen or other protein molecules of the tissue.

The results also indicate that tissue having a shrinkage temperature close to fresh tissue is degraded by collagenase to a greater extent than tissue having higher shrinkage temperature. It can be seen that an increase in shrinkage temperature of only 4 to 5° C. leads to tissue that is resistant to collagenase, which is evidence of substantial cross-linking.

EDC sterilization in HEPES buffer containing 20% isopropyl alcohol, carried out either in the presence or in the absence of tissue, leads to complete kill of the spores Bacillus subtilis. The following experiment was designed to test whether the sterilization efficacy of EDC remains substantially unaffected by the presence of cross-linking agents. Approximately 1.7×10$^5$ spores were inoculated in glass ampoules, 5 samples per condition. After 10 minutes, 10 mL of Solutions A, B, C, D, E and F containing 25 mM EDC were added, the ampoules were heat-sealed and placed at 40° C. After 24 hours, the solutions from the ampoules were filtered to recover the spores, the filters were washed with 0.1% peptone water, and these were incubated on TSA plates for up to 10 days at 32° C. to 33° C., after which the colonies were enumerated. The positive and the negative controls were shown to validate the test. The results are presented in Table 2C.

TABLE 2C

| BLOCKING AGENT | SURVIVORS # CFAs |
|---|---|
| NH$_4$Cl | 0 |
| Hydroxyproline | 0 |
| TRIS | 0 |
| Ethanolamine | 0 |
| TRIS + Ethanolamine | 0 |
| HEPES Control | 0 |
| Negative Control | − |
| Positive Control | + |

The results indicate that the presence of cross-linking blocking agents has no effect on the sterilization efficacy of EDC.

EXAMPLE 4

In Example 3, the solution containing 50 mM TRIS plus 50 mM ethanolamine was shown to exhibit the greatest protection against the formation of zero length cross-links. The following experiment was designed to test the effect of different concentrations of TRIS and ethanolamine on the cross-linking protection of porcine pericardium. The concentrations used were TRIS 0 mM and ethanolamine 0 mM (HEPES buffer control); TRIS 25 mM and ethanolamine 25 mM; TRIS 50 mM and ethanolamine 50 mM; and TRIS 100 mM and ethanolamine 100 mM; all contained 20% isopropyl alcohol. Sheets of porcine pericardium were sterilized in the solutions mentioned above in the presence of 25 mM EDC at 40° C. After 24 hours, the samples were removed and placed at room temperature. The porcine pericardium stability to thermal denaturation and its resistance to collagenase digestion were tested as before. The results are set forth in Tables 3A and 3B.

TABLE 3A

| CONDITIONS | THERMAL DENATURATION ° C. mean +/- SEM |
|---|---|
| TRIS 25, ethanolamine 25 | 68.3 +/- 0.4 |
| TRIS 50, ethanolamine 50 | 67.4 +/- 0.7 |
| TRIS 100, ethanolamine 100 | 65.6 +/- 0.5 |
| HEPES Control | 73.0 +/- 0.2 |
| Fresh Tissue | 69.2 +/- 0.1 |

The results of the thermal denaturation show that increases in TRIS and ethanolamine concentrations lead to increased protection of cross-linking during sterilization, whereas an increase of 4° C. is observed in the absence of any cross-linking blocking agent.

A test with respect to collagenase digestion was also carried out as described for Example 3, but the collagenase concentration used was approximately 187 units of collagenase per test. The incubation duration was 72 hours at 37° C., and the results are presented in Table 3B.

TABLE 3B

| CONDITIONS | COLLAGENASE DIGESTION % WEIGHT DIGESTED mean +/− SEM |
|---|---|
| TRIS 25, ethanolamine 25 | 38.5 +/− 0.6 |
| TRIS 50, ethanolamine 50 | 73.2 +/− 1.3 |
| TRIS 100, ethanolamine 100 | 82.3 +/− 0.4 |
| HEPES Control | 5.7 +/− 0.4 |
| Fresh Tissue | 84.6 +/− 0.8 |

The results of collagenase digestion indicate that tissue sterilized in the absence of blocking agents, i.e. HEPES control, is highly resistant to collagenase digestion, which is evidence that it exhibits the highest cross-linking density. The resistance to cross-linking increases with increasing TRIS +ethanolamine concentrations to reach a level close to that of fresh tissue, showing the amount of resistance can be carefully controlled through the use of varying concentrations. Sterilization in the presence of ethanolamine at a concentration higher than 50 mM in HEPES buffer but without TRIS may also provide very good protection against cross-linking.

EXAMPLE 5

Following the completion of Example 4, it was decided to determine whether there would be any difference in the effect of the treatment upon porcine aortic valve leaflets as compared to pericardium.

Mixtures of TRIS (25 mM) plus ethanolamine (25 mM) and TRIS (100 mM) plus ethanolamine (100 mM) were used to sterilize porcine aortic valve leaflets and porcine pericardium. The samples were incubated for 24 hours at 40° in the above-mentioned solutions containing 25 mM EDC and 20% isopropyl alcohol. The control conditions were HEPES buffer+20% isopropyl alcohol with or without 25 mM EDC and fresh untreated porcine aortic valve leaflets. The thermal denaturation temperature and the stability to collagenase digestion were tested for each group of five samples. The results are presented in Table 4.

The results of this experiment confirm that TRIS plus ethanolamine buffers protect against cross-linking in both porcine aortic valve leaflets and porcine pericardium. The protection increases with the concentration of cross-linking blocking agents, and TRIS 100 mM plus ethanolamine 100 mM fully prevents zero length cross-linking of the tissue as can be seen in comparison to the HEPES+EDC control. In addition, it can be seen that the level of cross-linking, as assessed by collagenase, can be modulated by modification of the concentration of the blocking agents as indicated with reference to Example 4.

EXAMPLE 6

The testing reported in Table 2C of Example 3 was further pursued by adding pericardium to the tests. Five porcine pericardium coupons (5×5 cm) for each condition were placed in sterile cups and inoculated with $1.2 \times 10^6$ (6.08 Log) spores of *Bacillus subtilis*. After 10 minutes, 50 ml of the following solutions containing 25 mM EDC were poured onto the coupons and incubated at 40° C.:

HEPES 10 mM, NaCl 60 mM and $NH_4Cl$ 50 mM.

HEPES 10 mM, NaCl 70 mM and hydroxyproline 40 mM.

TRIS 50 mM and NaCl 70 mM.

HEPES 10 mM, ethanolamine 50 mM and NaCl 60 mM.

TRIS 25 mM, ethanolamine 25 mM and NaCl 70 mM.

TRIS 50 mM, ethanolamine 50 mM and NaCl 20 mM.

TRIS 100 mM, ethanolamine 100 mM.

HEPES 10 mM, NaCl 110 mM. (Control)

After 24 hours, the solutions were filtered through Millipore filter funnels, rinsed with 50 ml of 0.1% peptone water and plated onto TSA plates. The porcine pericardium coupons were washed for 20 minutes while shaking at 150 rpm with 50 ml of 0.1% peptone water solution containing 1 ml per liter of Tween 80. The solutions were filtered and the membranes were plated onto TSA plates. The TSA plates were incubated for 15 days at 32–33° and enumerated. The number of colony forming units (CFUs) for the solution and the pericardium coupons were added and the Log reduction determined. The positive and negative control were shown to validate the test, the results of which are presented in Table 5.

TABLE 4

| CONDITIONS | THERMAL DENATURATION ° C. mean +/− SEM (n = 5) | COLLAGENASE DIGESTION % WEIGHT DIGESTED (n = 5) |
|---|---|---|
| | Porcine aortic cusps | |
| TRIS 25+ Ethanolamine 25 | 66.5 +/− 0.6 | 30.1 +/− 1.5 |
| TRIS 100+ Ethanolamine 100 | 63.4 +/− 0.1 | 65.0 +/− 1.3 |
| Control HEPES without EDC | 66.2 +/− 0.3 | 65.9 +/− 3.1 |
| Control HEPES with EDC | 73.1 +/− 0.2 | 7.1 +/− 0.3 |
| Fresh cusps | 63.7 +/− 0.6 | 82.0 +/− 1.6 |
| | Porcine pericardiwn | |
| TRIS 25+ Ethanolamine 25 | 68.0 +/− 0.7 | 49.6 +/− 4.8 |
| TRIS 100+ Ethanolamine 100 | 64.3 +/− 1.4 | 82.7 +/− 0.6 |
| Control HEPES without EDC | 68.6 +/− 0.5 | 84.3 +/− 1.9 |
| Control HEPES with EDC | 72.1 +/− 1.1 | 5.8 +/− 1.0 |
| Fresh pericardium | 67.1 +/− 0.3 | 84.3 +/− 1.9 |

TABLE 5

| CONDITIONS | Log reduction of spores (n = 5) Solution plus tissue |
|---|---|
| NH$_4$Cl | 6.08 |
| Hydroxyproline | 6.08 |
| TRIS | 6.08 |
| Ethanolamine 50 | 6.08 |
| TRIS 25 + Ethanolamine 25 | 6.08 |
| TRIS 50 + Ethanolamine 50 | 6.08 |
| TRIS 100 + Ethanolamine 100 | 6.08 |
| Control HEPES | 5.97 |

The results indicate that sterilization occurs in the presence of cross-linking blocking agents, and they strongly support the concept that collageneous tissue and tissue-engineered scaffolds can be sterilized in the presence of cross-linking blocking agents to reach cross-linking density suitable for "time-controlled" resorbtion and potential remodeling after implantation in the human body. This method is also suitable for sterilization of tissue-derived devices where increased cross-linking of the tissue may be detrimental to the particular devise.

The tests thus show that the increased concentration of blocking agents leads to increased protection against cross-linking.

In addition, both amine-reactive agents (i.e. hydroxyproline) and carboxyl-reactive agents (i.e. ethanolamine, isopropyl amine etc.) provide protection against cross-linking of the tissue during sterilization with EDC. Other examples of amine-reactive agent are salts of lactic acid, acetic acid and salts of monocarboxylic acid. A concentration of monocarboxylic acid is chosen so as not to deplete EDC before complete sterilization is achieved.

Although the blocking agents described above may be best suited during sterilization, other carboxyl or amine-blocking agents can be reacted with tissue amine or carboxyl groups before sterilization. Examples of such agents include citraconic anhydride, acetic anhydride, maleic anhydride and N-hydroxysulfosuccinimide acetate.

It is also believed that it may be important to choose blocking agents that are able to readily diffuse within the proteinaceous material to carry out the desired modification in a reasonable time frame. For example, TRIS may be suitable for use in the treatment of a loose collagen structure such as collagen sponges and some collagen solution or suspension, but may not be suitable for the sterilization of a tighter structure, such as porcine pericardium.

The results generally indicate that an aqueous solution of EDC in the presence of a protecting agent for complexing with potentially reactive amine or carboxyl moieties on biological tissue, with or without 20% isopropyl alcohol (IPA), at about 40° C., is a powerful bactericide against spores of Bacillus subtilis and other bacteria although the inclusion of IPA is preferred. It is accordingly believed that such sterilization treatment using a water-soluble coupling agent in the presence or absence of isopropyl alcohol at a temperature above room temperature retains its potent bactericidal effect even though a protecting agent is present in an effective amount to prevent substantial cross-linking of biological tissue. Accordingly, such treatment is considered to be excellently suited for sterilization of allografts, e.g. tendons, ligaments, menici, vascular grafts and the like, and tissue valves, as the presence of such an effective amount of protecting agent adequately prevents a substantial and controllable rise in shrinkage or denaturation temperature and resistance to collagenase that is indicative of an extent of cross-linking such as might be undesirable in allografts or certain tissue valves.

Although the invention has been described with regard to certain preferred embodiments which constitute the best mode presently known by the inventors for carrying out the invention, it should be understood that changes and modifications that would be obvious to one having the ordinary skill in this art may be made without departing from the scope of the invention which is set forth in the claims appended hereto. For example, although the invention has been described with regard to the sterilization of tissue valve material and tendons and the like, it may also be used to sterilize other allografts for implantation within the human body. Although the use of a carbodiimide coupling agent is shown to be effective without the inclusion of a coupling enhancer, an enhancer such as N-hydroxysuccinimide (NHS) may be included. Although it is believed that the most feasible combinations of temperature, concentration and duration of incubation are disclosed, it should be understood that equivalently lower temperature and/or concentrations might be used with progressively longer durations of incubation.

The disclosures of the previously mentioned U.S. patents are expressly incorporated herein by reference.

Particular features of the invention are set forth in the claims which follow.

What is claimed is:

1. A process for sterilization of biological tissue material, which process comprises
    treating such material with an aqueous solution containing
        (a) an amount of a water-soluble coupling agent capable of creating amide bonds that is effective to achieve sterilization and
        (b) an amount of a protecting agent which is effective to complex with potentially reactive amine or carboxyl moieties on the biological tissue material so as to deter such complexed moieties from taking part in an amide-forming cross-linking reaction and thereby limit the amount of cross-linking, and
    maintaining such treatment for a time and at a temperature which is sufficient to achieve penetration of said coupling agent into the cells of microorganisms carried by such material and effectively kill such microorganisms.

2. The process for sterilization according to claim 1 wherein said coupling agent is present in said solution at a concentration of at least about 25 mM.

3. The process for sterilization according to claim 2 wherein said treatment is carried out at a temperature of about 25° to about 55° C. in the presence of an effective amount of a lower alkanol.

4. The process for sterilization according to claim 2 wherein said treatment is carried out at a temperature of at least about 35° C. in the absence of any effective amount of a lower alkanol and said treatment is carried out for at least about 24 hours.

5. The process for sterilization according to claim 2 wherein said protecting agent is present in said aqueous solution at a concentration of at least about 25 mM.

6. The process for sterilization according to claim 5 wherein said protecting agent includes a monoamine.

7. The process for sterilization according to claim 5 wherein said protecting agent includes a monocarboxylic acid.

8. The process for sterilization according to claim 1 wherein said coupling agent is present in said solution at a concentration of at least about 35 mM and said protecting agent is present at a concentration between about 50 and about 150 mM.

9. The process for sterilization according to claim 8 wherein said treatment is carried out for at least about 6 hours.

10. The process for sterilization according to claim 1 wherein said coupling agent is EDC which is present at a concentration of at least about 50 millimolar and said treatment is carried out for at least about 10 hours at a temperature of at least about 40° C.

11. A process for sterilization of biological tissue, which process comprises treating such biological tissue at a temperature of at least about 35° C. with an aqueous solution containing an effective amount of a lower alkanol and a concentration of at least about 25 mM of a water-soluble coupling agent that is capable of creating amide bonds and maintaining said treatment, in the presence of an effective amount of a protecting agent which complexes with either amine or carboxyl moieties and thereby deters cross-linking, for a period so as to effectively kill any bacteria and spores carried by such biological tissue, whereby contemporaneous cross-linking of the biological material can be controlled as desired.

12. The process for sterilization according to claim 11 wherein said aqueous solution contains said protecting agent at a concentration of between about 50 and about 150 mM.

13. The process for sterilization according to claim 11 wherein said protecting agent includes either a monoamine or a monocarboxylic acid.

14. The process for sterilization according to claim 11 wherein said solution contains EDC as said water-soluble coupling agent at a concentration of at least about 35 mM, wherein said treatment is carried out at between 40° C. and about 50° C. and wherein said treatment is carried out in the presence of at least about 50 mM of ethanolamine.

15. The process for sterilization according to claim 14 wherein said solution also contains at least about 50 mM of TRIS.

16. A process for sterilization of biological tissue material, which process comprises treating such material with a protecting agent which is effective to complex with potentially reactive amine or carboxyl moieties on the biological tissue material so as to deter such complexed moieties from taking part in an amide-forming cross-linking reaction and thereby limit the amount of cross-linking, treating such material with a water-soluble coupling agent capable of creating amide bonds that is effective to achieve sterilization, and maintaining such treatment with said coupling agent for a time and at a temperature which is sufficient to achieve penetration of said coupling agent into the cells of microorganisms carried by such material and effectively kill such microorganisms.

17. The process for sterilization according to claim 16 wherein said coupling agent and said protecting agent are present in an aqueous solution being used for said treatment.

18. The process for sterilization according to claim 17 wherein said protecting agent includes hydroxyproline, lactic acid or acetic acid.

19. The process for sterilization according to claim 17 wherein said biological tissue material is pretreated with said protecting agent at a concentration of at least about 10 mM and then rinsed before treatment with an aqueous solution of said coupling agent.

20. The process for sterilization according to claim 19 wherein said protecting agent is sulfo-NHS acetate, acetic anhydride, maleic anhydride or citraconic anhydride.

* * * * *